United States Patent [19]

Bowden

[11] Patent Number: 4,655,234

[45] Date of Patent: Apr. 7, 1987

[54] DENTAL FLOSS HOLDING TOOL

[76] Inventor: J. Claude Bowden, P.O. Box 7596, Klamath Falls, Oreg. 97602

[21] Appl. No.: 740,538

[22] Filed: Jun. 3, 1985

[51] Int. Cl.⁴ .............................................. A61C 15/00
[52] U.S. Cl. ................................ 132/92 A; 132/92 R
[58] Field of Search ............... 132/92 R, 89, 90, 91, 132/92 A, 93

[56]  References Cited

U.S. PATENT DOCUMENTS

| | | | |
|---|---|---|---|
| 725,462 | 4/1903 | Luallen | 132/92 A |
| 2,163,500 | 6/1939 | Shepard | 132/92 R |
| 2,724,390 | 11/1955 | Sokoloski | 132/92 R |
| 2,872,929 | 2/1959 | Rice | 132/91 R |
| 3,340,881 | 9/1967 | Cowan | 132/92 A |
| 3,376,876 | 4/1968 | Wicklund | 132/92 R |
| 3,592,203 | 7/1971 | Johnson | 132/91 |
| 3,734,107 | 5/1973 | Thierman | 132/92 A |
| 3,746,017 | 7/1973 | Casselman | 132/92 A |

FOREIGN PATENT DOCUMENTS 2074876  11/1981  United Kingdom ............. 132/92 A Primary Examiner—John J. Wilson
Attorney, Agent, or Firm—Eugene M. Eckelman

[57] ABSTRACT

A body member has a recess arranged to hold a spool of dental floss. A hollow shank projects integrally from the forward end of the body member and is arranged to receive floss therein. The shank is turned downwardly in a tip end and forms a spanning area with the front of the body member. Anchor points are provided at the tip of the shank and on the body member for engagement by the floss to hold it tight across the spanning area. The body member has a flat lower edge and a contoured upper edge to provide a firm grip by the palm and fingers of the hand.

1 Claim, 3 Drawing Figures

DENTAL FLOSS HOLDING TOOL

BACKGROUND OF THE INVENTION

This invention relates to new and useful improvements in dental floss holding tools.

Various types of dental floss holding tools have heretofore been patented and primarily comprise a handle portion and a shank which provides some sort of spanning area for dental floss whereby the floss in the spanning area can be manipulated between the teeth for flossing. One disadvantage of previous flossing tools is that they are complex in structure which makes them expensive to manufacture and difficult to operate. Another disadvantage of previous flossing tools is that the spanning area of most of them comprises a pair of notched fingers which do not hold the floss sufficiently in place or tight enough to prevent it from displacement under hard flossing conditions. Still another disadvantage of prior tools is that the spanning area for the floss is not located such that the tool can be conveniently manipulated to reach the spaces between all the teeth.

SUMMARY OF THE INVENTION

According to the present invention and forming a primary objective thereof, a dental floss holding tool is provided that is simplified in structure and inexpensive to manufacture.

Another object of the invention is to provide a dental floss holding tool wherein the floss cannot slip from holding fingers or the like during hard flossing conditions.

Another object is to provide a dental floss holding tool having a design which locates the spanning area for the floss in a position such that all areas of the teeth are readily accessible.

In carrying out these objectives, the dental floss holding tool comprises a body member contoured for firm and convenient gripping in the hand. A hollow shank projects from an upper portion of the forward end of the body member in longitudinal alignment therewith, and the outer end of the shank is turned downwardly in a tip end to form a spanning area between the tip and a lower portion of the forward end of the body member. One side of the body member is recessed to hold a spool of floss, and means are provided in the body member and the shank to direct floss from the spool in the body member through the hollow shank and out the tip of the shank and then across a spanning area. Anchor means are provided on the nozzle end and the lower front end of the body member to hold the floss tight.

The invention will be better understood and additional objects and advantages will become apparent from the following description taken in connection with the accompanying drawings.

DETAILED DESCRIPTION OF A PREFERRED EMBODIMENT

Figure 1:
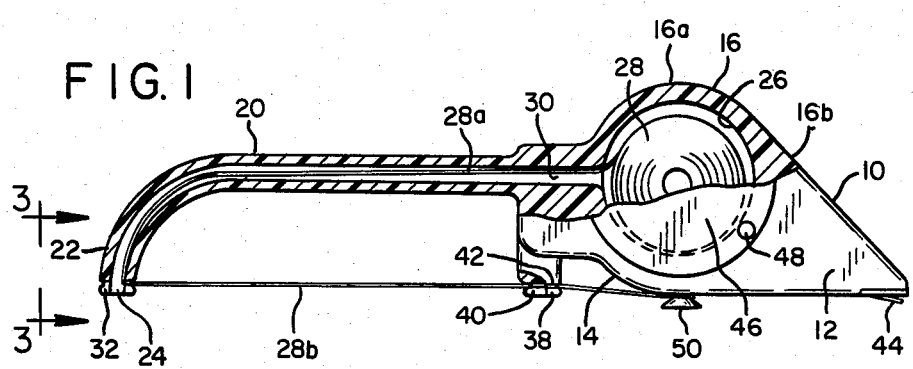
FIG. 1 is a side elevational view, partly broken away, of the dental floss holding tool embodying features of the present invention.
Figure 2:
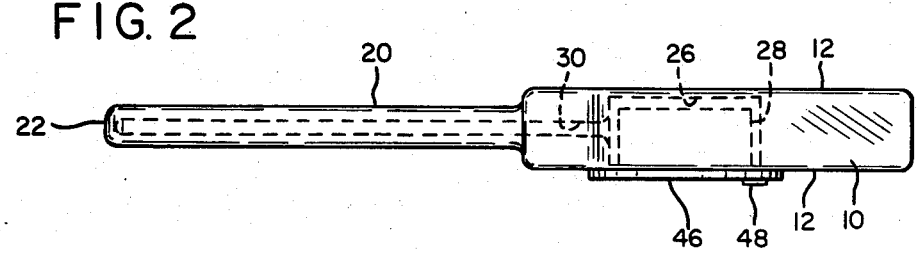
FIG. 2 is a top plan view of the tool.

With particular reference to the drawings, the present dental floss holding tool comprises a body member 10 having flat, parallel side surfaces 12 in a plate-like construction, and also having a bottom edge 14 and a top edge 16. The bottom edge, throughout most of its length, is substantially flat whereby to lie flatwise across the hand when the device is gripped. The top edge 16 has a forward rounded contour 16a which leads into a straight portion 16b extending downwardly at an angle to the bottom edge at the rear. The flat portion of the bottom edge 14 allows the tool to lie flatwise in the palm of the hand or fingers and the contoured top edge 16 allows a good firm grip on the top by the fingers.

A hollow shank or nozzle 20 leads integrally from an upper portion of the front of the body member 10 and has a forward, downwardly turned tip portion 22 terminating in substantially the plane of the flat portion of the bottom edge and having a bottom opening 24. One side of the body member has a recess 26 arranged to receive a spool 28 of dental floss. An opening 30 leads between the rearward portion of the shank 20 and the recess 26, and floss 28a from the spool 28 in the recess is arranged to be directed through this opening into the hollow shank and out the tip opening 24.

Figure 3:
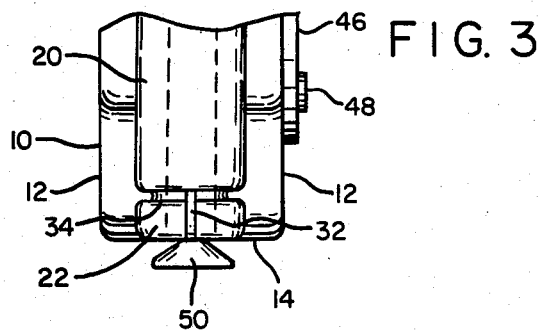
FIG. 3 is a fragmentary front elevational view taken on the line 3—3 of FIG. 1.

Anchor means are provided at the tip of the shank and on the bottom of the body member 10 to hold the floss tight across a spanning area or section 28b of the floss. The anchor means at the tip of the shank comprises a narrow vertical slot or slit 32, FIG. 3, leading up from the lower surface of the tip into which the floss can be fitted at the one end of the spanning area 28b. Slot 32 is of small width whereby to obtain a frictional grip on the floss. In addition, a narrow horizontal groove 34 disposed in the plane of slot 32 is provided around the tip of the shank whereby the floss after having been fitted in a portion of the slot 32 can be wrapped around the post in the groove 34 one or more times to provide a firm anchored grip. The anchor means at the rear of the spanning area 28b comprises a post 38 on the bottom front of the body member. Such post has similar floss attaching means as the tip of the shank, comprising a narrow vertical groove 40 and a narrow horizontal slot 42, the floss after having been fitted in a portion of the slot 40 then wrapped around the post to anchor the floss at this end of the spanning area. The upwardly extending slots 32 and 40 terminate at the respective grooves 34 and 42.

A further anchoring post 50 is provided between the post 38 and the cutter 44. This post comprises a tapered button type member around which a tag end of the floss from post 38 can be wrapped. Although the anchor means at the opposite ends of the spanning area 28b adequately hold the floss tight, the post 50 is extra insurance that this end of the floss will be held tight.

The rearward end of the tool on the bottom edge has a cutter 44 of conventional construction for severing used portions of the floss.

Recess 26 is closed by a cover 46 hinged at 48. This cover provides access for the purpose of loading a new spool in the recess 26 and when in position holds the spool in place.

As apparent, the present floss holder is simplified in construction and inexpensive to manufacture. Since the floss is directed through a hollow shank and is positively confined at both ends of the spanning area, it is not possible for the floss to slip out of position, even under hard flossing conditions. The spanning area provides ready access to all areas of the teeth. That is, the tool can readily reach the front teeth and the shank can be employed to readily displace rear portions of the mouth to reach rear teeth. The contour of the body member, as stated above, allows a good grip for manipulation of the tool in the mouth.

It is to be understood that the form of my invention herein shown and described is to be taken as a preferred example of the same and that various changes in the shape, size and arrangement of parts may be resorted to without departing from the spirit of my invention, or the scope of the subjoined claims.

Having thus described my invention, I claim:

1. A dental floss holding tool comprising a plate-like handle arranged to be gripped in the hand, said handle having upper and lower edges, forward and rearward ends, and parallel said walls, a portion of the lower edge of said handle being flat for lying in the palm of the user's hand and the upper edge being rounded upwardly for a firm cupped engagement by the user's fingers;

a hollow shank projecting from an upper portion of the forward end of said handle in longitudinal alignment with said handle, said shank having an outer free end, said outer free end being turned downwardly to a tip end terminating in substantially the plane of the flat lower edge of said handle to form a spanning area between it and said handle;

recess means in said handle arranged to hold a spool of floss;

floss outlet means in said handle communicating between said recess means and said hollow shank for directing floss upwardly into said shank from a spool in the recess;

and releasable anchor means on said tip end and on said body member arranged for engagement by the floss to hold it across said spanning area for flossing the teeth, said releasable anchor means comprisng an anchor post on said tip end and an anchor post on a forward portion of a lower end of said handle, each of said anchor posts including a peripheral groove extending around said posts in spaced relation from the tip end and a longitudinal slit leading upwardly from said tip end and terminating at said peripheral groove, said slits being of a dimension to frictionally grip floss forced thereinto whereby the span of floss between said posts is arranged to be held tightly by engagement around said posts in said peripheral grooves and in said slits, and a second anchor post on the lower edge of said handle spaced rearwardly from the first mentioned post on said body member for further anchored engagement of the floss.

* * * * *